US00PP18278P2

(12) United States Plant Patent
Evers

(10) Patent No.: US PP18,278 P2
(45) Date of Patent: Dec. 4, 2007

(54) ROSE PLANT NAMED 'TAN97274'

(50) Latin Name: *Rosa hybrida L.*
Varietal Denomination: TAN97274

(75) Inventor: Hans Jürgen Evers, Uetersen (DE)

(73) Assignee: Rosen Tantau Mathias Tantau Nachfolger, Uetersen (DE)

( * ) Notice: Subject to any disclaimer, the term of this patent is extended or adjusted under 35 U.S.C. 154(b) by 0 days.

(21) Appl. No.: 11/251,072

(22) Filed: Oct. 14, 2005

(30) Foreign Application Priority Data

Jun. 14, 2006 (EP) ..... 2006/1259

(51) Int. Cl.
*A01H 5/00* (2006.01)

(52) U.S. Cl. ..... Plt./107

(58) Field of Classification Search ..... Plt./107, Plt./101, 108
See application file for complete search history.

(56) References Cited

PUBLICATIONS

GTITM UPOV ROM Citation for 'TAN97274' as per QZ PBR 2002–0378; Mar. 11, 2002.*

* cited by examiner

*Primary Examiner*—Kent Bell
(74) *Attorney, Agent, or Firm*—Klarquist Sparkman LLP

(57) ABSTRACT

Rose plant having high resistance to black spot and powdery mildew.

4 Drawing Sheets

Genus and species: *Rosa hybrida L.*
Varietal Denomination: 'TAN97274' (Sweet Haze™).

ORIGIN OF THE INVENTION

The present invention relates to a new and distinct variety of bed rose plant, which was originated by me by crossing the variety 'Tandalaum' (not patented) with the variety 'Mainaufeuer' (not patented).

BACKGROUND OF THE INVENTION

The primary objective of this breeding was to produce a new rose variety having high resistance to black spot and powdery mildew.

BRIEF SUMMARY OF THE INVENTION

The objective was substantially achieved, along with other desirable improvements that will become apparent hereinafter.

Asexual reproduction of this new variety by budding, as performed at Uetersen, Germany, shows that the foregoing and all other characteristics and distinctions come true to form and are established and transmitted through succeeding propagations.

Comparison with Parents

The seed parent plant, 'Tandalaum', the most similar variety, has crème-white flowers whereas the petals of TAN97274 are light pink. The pollen parent, 'Mainaufeuer', has red flowers (RHS 44B). Another similar variety is 'Tandaltex' which has a broad and bushy growth habit and slightly concave leaflets as compared to the narrow bushy growth habit and convex leaflets of 'TAN97274'.

BRIEF DESCRIPTION OF THE ILLUSTRATIONS

The accompanying illustrations show typical specimens of flowers of this new variety depicted in color as nearly true as it is reasonably possible to make the same in a color illustration of this character.

Figure 1:
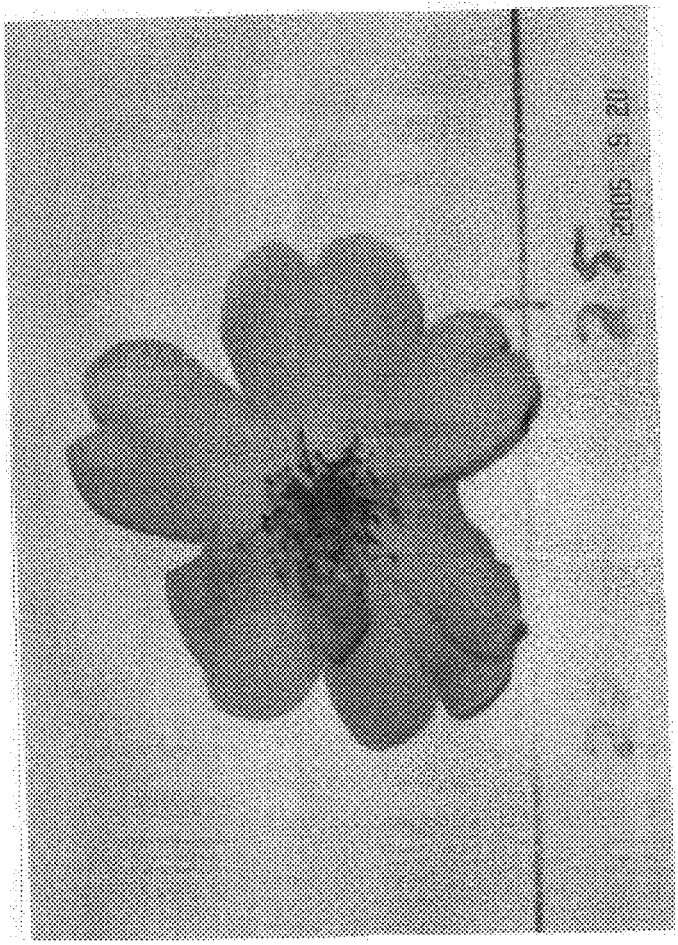
FIG. 1 is top view of an open blossom.
Figure 2:
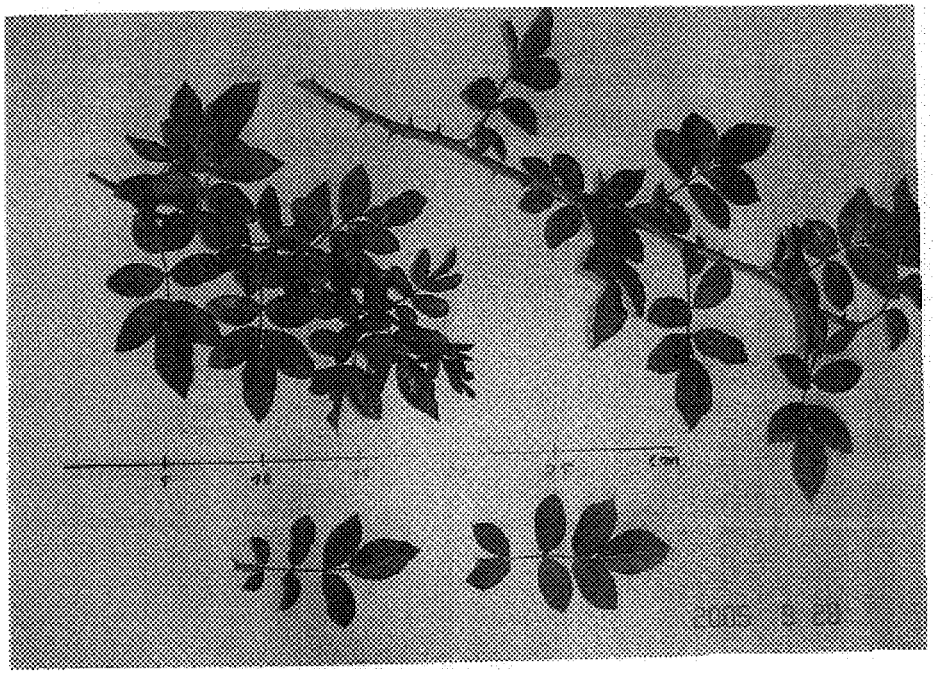
FIG. 2 is a view showing a stem with attached leaves; a detached leaf; and detached leaflets.
Figure 3:
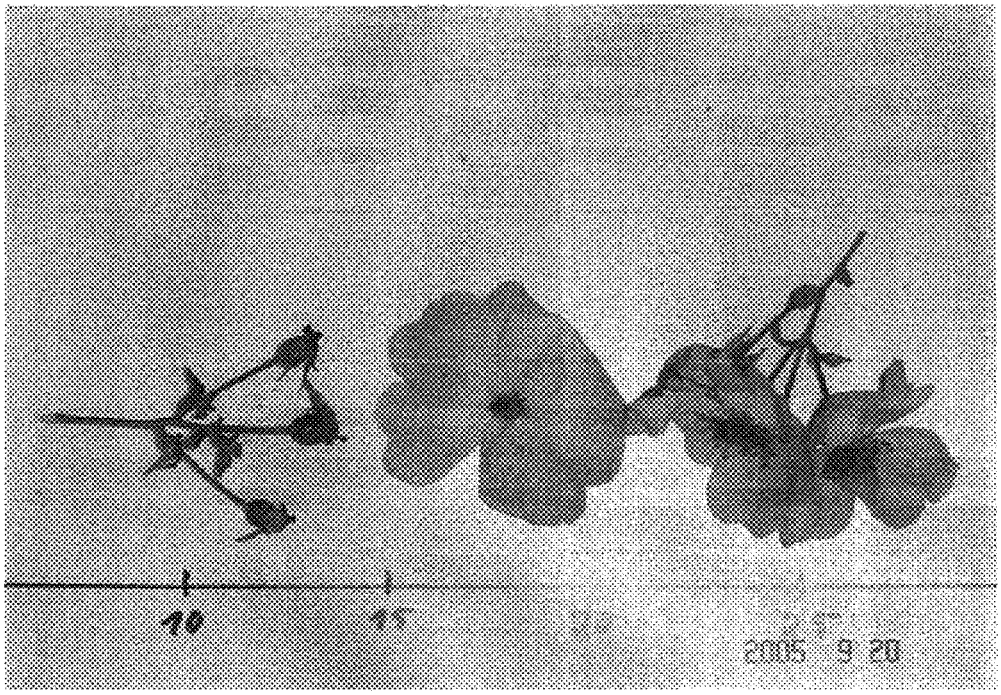
Figure 4:
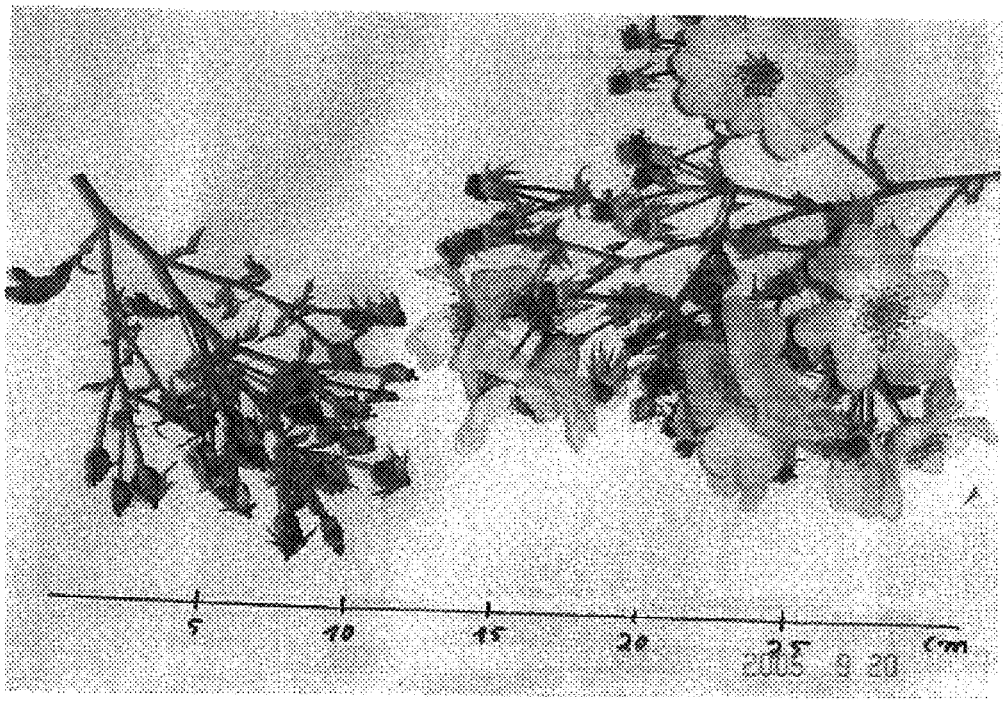
Figure 5:
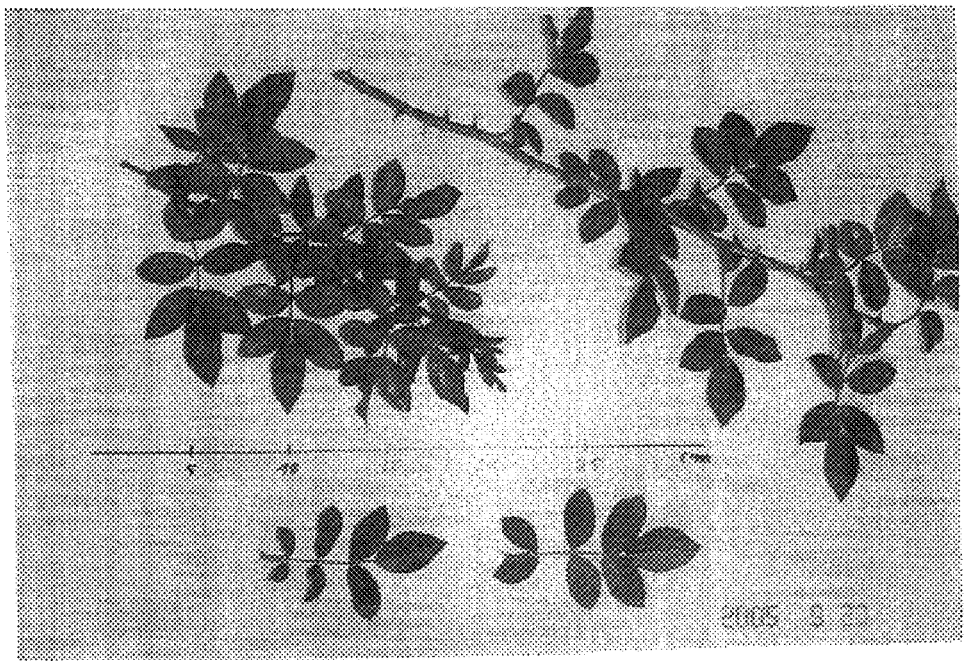
Figure 6:
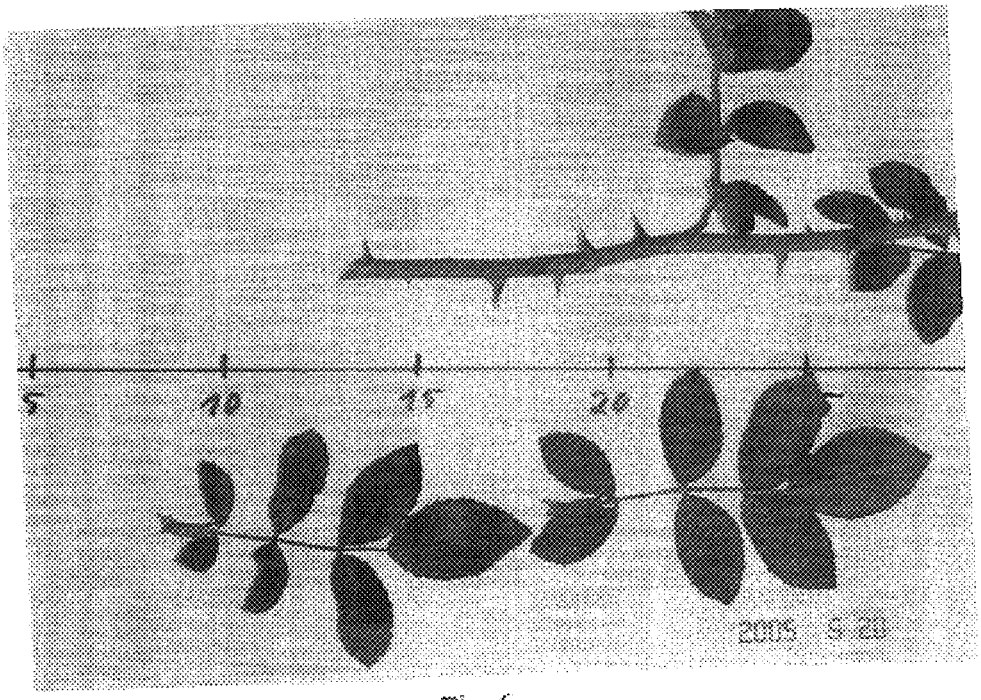

FIG. 3 contains views showing the end of a flower stem with attached hips; the underside of an open flower; and a typical open flower cluster;

FIG. 4 contains views showing a typical cluster of flower buds and showing a cluster containing flower buds, open flowers and flowers after petal drop;

FIGS. 5 and 6 are further views of the stems, leafs, and leaflets; and

Figure 7:
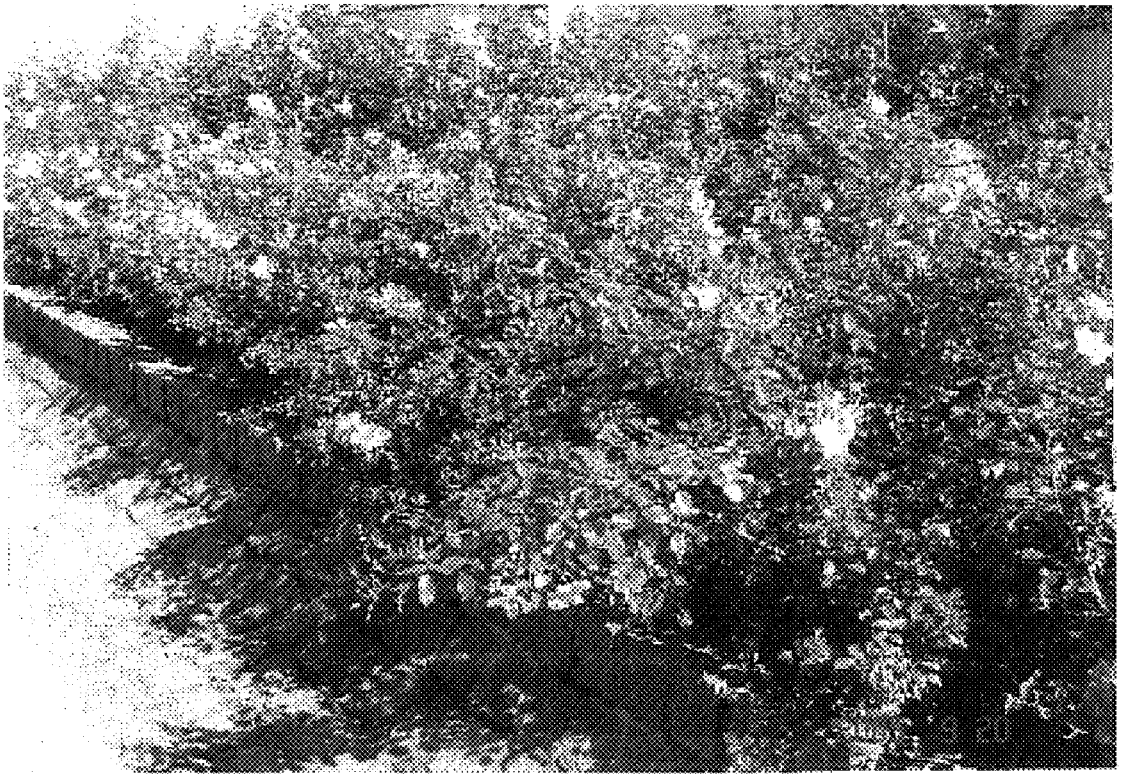

FIG. 7 is a view of a bed of the rose plants of the application.

DETAILED BOTANICAL DESCRIPTION

The following is a detailed description of my new rose cultivar with color descriptions using terminology in accordance with The Royal Horticultural Society (London) Colour Chart (1996), except where ordinary dictionary significance of color is indicated.

Observations made are of plants of three years of age grown in a garden environment in Northern Germany.

Parentage:
*Seed parent.*—'Tandalaum' (Traumland™).
*Pollen parent.*—'Mainaufeuer'.

FLOWER

Blooming habit: Continuous.

Bud:

*Size.*—About 1.8 cm long and 1.1 cm in diameter when the petals start to unfurl.

*Form.*—Blunt topped and broad ovate in longitudinal section.

*Color.*—When sepals first divide, bud color is Red Group 55B. When half blown, the upper sides of the petals are Red Group 55C; and the lower sides of the petals are Red Group 56A.

*Sepals.*—Color: Upper surface: Green Group 138B. Lower surface: Green Group 138B. Length: 1.4 cm. Width: 0.3 cm. Shape: Elongate, pointed. Surface texture: Smooth. There are three lightly appendaged sepals. There are two unappendaged sepals with smooth edges.

*Receptacle.*—Color: Green Group 143A. Shape: Pear. Size: Medium, about 1.2 cm diameter. Surface: Smooth.

*Peduncle.*—Length: Medium, averaging about 3 cm. Diameter: 0.5 cm. Surface: Prickly. Color: Surface: Yellow-Green Group 144B. Prickles: Red Group 53A. Strength: Erect.

Bloom:

*Size.*—Medium. Average open diameter is about 7.3 cm. Depth: 0.9 cm.

*Borne.*—In flat clusters of 14 blooms.

*Stems.*—Strength: Weak. Average length is about 40 cm and diameter 1.2 cm.

*Form.*—When first open: Almost flat. Permanence: Flattens further.

*Petalage.*—Number of petals under normal conditions: 7.

*Color.*—The upper sides of the petal are Red Group 55A. The reverse sides of the petals are Red Group 55C. The base of the petals has a small white spot, White Group 155A. The major color on the upper side is Red Group 55A.

*Variegations.*—None.

*Discoloration.*—The general tonality at the end of the first day is Red Group 55B and by the end of the third day brightens to Red Group 55D. Color brightens with age.

*Fragrance.*—None.

Petals:

*Texture.*—Thin.

*Surface.*—Smooth.

*Shape.*—Oval.

*Margin.*—Smooth.

*Apex shape.*—Blunt, oval.

*Base shape.*—Blunt, oval.

*Form.*—Tips slightly recurved.

*Arrangement.*—Quartered.

*Petaloids.*—Number: 2. Color: Red Group 55B.

*Persistence.*—Petals drop off cleanly before drying.

*Lastingness.*—On the plant: Short, about 10 days. As a cut flower: Short, about 3 days.

Reproductive parts:

*Stamens.*—Number: 103. Length: 0.7 cm. Anthers: Length: 0.1 cm. Color: Orange Group 26A. Arrangement: Regular around styles. Filaments: Color: Orange-Red Group 34C. Length: 0.6 cm. Pollen: Color: Orange Group 27A.

*Pistils.*—Number: 16. Length: 0.3 cm. Styles: Color: Red Group 42A. Length: 0.2 cm. Stigmas: Color: Yellow-Orange Group 23A. Length: 0.08 cm.

*Hips.*—Color: Red Group 45A. Shape: Globular. Size: Length and width 1.1 cm.

PLANT

*Form.*—Bush.

*Growth.*—Vigorous.

*Mature plant.*—Height: 80 cm. at 5 years. Width: 50 cm.

*Rootstock.*—*R. canina,* but may be propagated on own roots.

Foliage: Number of leaflets on normal mid-stem leaves: 5.

*Size.*—Small (10 cm long×6.8 cm wide).

*Quantity.*—Normal.

*Color.*—New foliage: Upper side: Green Group 143A. Lower side: Green Group 148B. Old foliage: Upper side: Green Group 147B. Lower side: Green Group 147C.

Leaflets:

*Size.*—About 3.7 cm long×1.9 cm wide.

*Shape.*—Elliptic.

*Base shape.*—Round.

*Apex shape.*—Pointed.

*Texture.*—Upper side: Leathery.

*Edge.*—Serrated.

*Serrations.*—Single.

*Petiole.*—Color: Green Group 146C. Length: 4 cm. Diameter 0.1 cm.

*Petiole rachis.*—Color: Green Group 146C overlaid with Orange-Red Group 30A. Underside: Green Group 146C overlaid with Orange-Red Group 30A. Length: 7.7 mm.

*Stipules.*—Serrated. Length: 0.9 cm.

*Auricles.*—Color: Green Group 146B; serrated.

*Disease resistance.*—Resistant to powdery mildew and blackspot in garden environment.

*Pest resistance.*—Not tested.

*Vein color.*—Green Group 138C.

*Venation pattern.*—Pyramidal net pattern.

Wood:

*New wood.*—Color: Green Group 146B. Bark: Smooth.

*Old wood.*—Color: Brown Group 164A. Bark: Rough.

*Canes.*—Length: 35 cm. Diameter: 0.63 cm. Internode Length: 3.05 cm.

Prickles:

*Quantity.*—On main canes from base: Few, four per stem.

*Form.*—Straight.

*Length.*—0.4 cm.

*Width.*—0.7 cm.

*Color when young.*—Greyed-Orange Group 168A.

*Color when mature.*—Brown Group 174A.

Small prickles:

*Quantity.*—On main stalks: None.

Winter hardiness: Known to be hardy to Zone 8B; may be hardier but not tested.

I claim:

1. A new and distinct variety of rose plant, substantially as herein shown and described, characterized particularly by its high resistance to black spot and powdery mildew.

* * * * *

UNITED STATES PATENT AND TRADEMARK OFFICE

CERTIFICATE OF CORRECTION

PATENT NO. : PP 18,278 P2
APPLICATION NO. : 11/251072
DATED : December 4, 2007
INVENTOR(S) : Hans Jurgen Evers It is certified that error appears in the above-identified patent and that said Letters Patent is hereby corrected as shown below:

Title page column 2, line 29, "(1996)" should read --(1966)--.

Signed and Sealed this

Twenty-third Day of December, 2008

JON W. DUDAS
*Director of the United States Patent and Trademark Office*